US012151839B2

(12) United States Patent
Lizari Illarramendi et al.

(10) Patent No.: US 12,151,839 B2
(45) Date of Patent: Nov. 26, 2024

(54) MACHINE FOR THE PREPARATION OF A MEDICAL PRODUCT WITH A REMOVABLE DEVICE FOR LOADING MEDICAL CONTAINERS AND METHOD FOR INTRODUCING THE REMOVABLE DEVICE INTO THE MACHINE

(71) Applicant: KIRO GRIFOLS, S.L., Arrasate (ES)

(72) Inventors: Borja Lizari Illarramendi, Arrasate (ES); Naiara Telleria Garay, Arrasate (ES); Patxi Urtzelai Aranbarri, Arrasate (ES); Jose Ignacio Andres Pineda, Arrasate (ES); Amaia Ilzarbe Andres, Arrasate (ES)

(73) Assignee: Kiro Grifols, S.L., Arrasate (ES)

( * ) Notice: Subject to any disclaimer, the term of this patent is extended or adjusted under 35 U.S.C. 154(b) by 0 days.

(21) Appl. No.: 18/321,666

(22) Filed: May 22, 2023

(65) Prior Publication Data

US 2024/0002083 A1 Jan. 4, 2024

(30) Foreign Application Priority Data

Jul. 1, 2022 (EP) .................................... 22382632

(51) Int. Cl.
| | |
|---|---|
| *B65B 43/54* | (2006.01) |
| *A61M 5/00* | (2006.01) |
| *A61M 5/178* | (2006.01) |
| *B65B 3/00* | (2006.01) |

(52) U.S. Cl.
CPC ............. *B65B 43/54* (2013.01); *A61M 5/008* (2013.01); *A61M 5/1782* (2013.01); *B65B 3/003* (2013.01)

(58) Field of Classification Search
CPC ......... B65B 3/003; B65B 3/006; B65B 43/42; B65B 43/54; A61M 5/008; A61M 5/1782
USPC ............................ 53/249; 141/237, 369, 378
See application file for complete search history.

(56) References Cited

U.S. PATENT DOCUMENTS

| | | | | |
|---|---|---|---|---|
| 2,100,039 | A | * 11/1937 | Standley ................. | B65B 43/54 141/369 |
| 2,193,059 | A | * 3/1940 | Chapman ................ | B65B 3/003 141/91 |
| 2,658,656 | A | * 11/1953 | Halahan et al. ........ | B65B 3/003 141/276 |

(Continued)

FOREIGN PATENT DOCUMENTS

| | | | |
|---|---|---|---|
| DE | 102018219400 A1 * | 5/2020 | ............. B65B 3/003 |
| ES | 2643119 B1 | 3/2018 | |

(Continued)

*Primary Examiner* — Stephen F. Gerrity
(74) *Attorney, Agent, or Firm* — Knobbe, Martens, Olson & Bear, LLP

(57) ABSTRACT

A machine is for the preparation of medical product. The machine includes a worktop for receiving containers. The worktop includes a series of holes for the introduction into each of them of an injection point belonging to a medical container to be filled. The holes give access to an interior of the machine, so that the injection points of the medical containers remain inside for their filling by the machine. The machine includes a removable device for loading medical containers into the machine. The removable device includes housings for the medical containers and detachable fasteners to the worktop of the machine.

14 Claims, 15 Drawing Sheets

(56) References Cited

U.S. PATENT DOCUMENTS

| | | | |
|---|---|---|---|
| 3,701,410 A * | 10/1972 | Shields | B65B 3/006 |
| | | | 198/740 |
| 3,713,771 A * | 1/1973 | Taylor et al. | A61B 10/0096 |
| | | | 422/534 |
| 3,785,773 A * | 1/1974 | Rohrbaugh | B01L 3/5085 |
| | | | 422/561 |
| 9,144,801 B2 * | 9/2015 | Johnson et al. | B01L 9/06 |
| D837,401 S * | 1/2019 | Gardner et al. | D24/230 |
| 10,478,820 B2 * | 11/2019 | Knight | G01N 35/10 |
| 11,260,400 B2 * | 3/2022 | Zhu et al. | B03C 1/288 |
| 2005/0133729 A1 * | 6/2005 | Woodworth et al. | A61M 5/008 |
| | | | 250/455.11 |
| 2008/0051937 A1 | 2/2008 | Khan et al. | |
| 2015/0335532 A1 * | 11/2015 | Lizari Illarramendi et al. | |
| | | | B65B 3/003 |
| | | | 141/27 |
| 2017/0144782 A1 | 5/2017 | Sisken et al. | |
| 2018/0016046 A1 * | 1/2018 | Miller | B65B 43/54 |
| 2019/0048303 A1 | 2/2019 | Maggiore | |
| 2019/0083360 A1 * | 3/2019 | Biehl et al. | A61J 3/002 |
| 2020/0147297 A1 | 5/2020 | Endyk | |
| 2021/0170092 A1 * | 6/2021 | Zhou et al. | A61M 5/008 |
| 2021/0292014 A1 * | 9/2021 | Trebbi et al. | B65B 3/003 |
| 2021/0309398 A1 | 10/2021 | Kircher et al. | |

FOREIGN PATENT DOCUMENTS

| | | | |
|---|---|---|---|
| KR | 20160027466 A | 3/2016 | |
| WO | WO-2022197181 A2 * | 9/2022 | B65B 3/003 |

* cited by examiner

MACHINE FOR THE PREPARATION OF A MEDICAL PRODUCT WITH A REMOVABLE DEVICE FOR LOADING MEDICAL CONTAINERS AND METHOD FOR INTRODUCING THE REMOVABLE DEVICE INTO THE MACHINE

CROSS-REFERENCE TO RELATED APPLICATION

This application claims priority to European Patent Application No 22382632.2 filed on Jul. 1, 2022, the disclosure of which including the specification, the drawings, and the claims is hereby incorporated by reference in its entirety.

FIELD OF THE INVENTION

The present application relates to a machine for the preparation of medical product, specifically a machine with a removable device for loading medical containers into said machine.

BACKGROUND OF THE INVENTION

Automated machines for the preparation of medical product, such as intravenous medication, and for filling or loading medical containers, i.e., containers with medical products, are already known on the market. An example of these machines are the dosing machines. These types of machines or devices are usually made up of a laminar flow cabinet and internal robotic means that carry out the necessary movements for the withdrawal of medicine from a source container and the injection of this medicine in final medical containers. The injection of the medical product in the medical containers is carried out through an injection or dosing point located in the medical container.

These machines may include a worktop with holes for introducing the dosing points of the medical containers. These holes may also be cavities in the worktop. Once introduced, the robotic means of the machine fill the different medical containers by introducing the medical product at a dosing point in the container. In this type of worktop dosing machine, the robotic means for filling the containers are located inside the machine, below the worktop and arranged below the containers so that the dosing point of the medical container is located below the worktop. Other types of dosing machines may use safety barriers that separate the load from the robotic means without using a worktop.

Dosing machines are usually designed for the filling of only one specific type of medical container and include supports for said type of container. Machines that allow different types of final medical containers to be supported thanks to the use of specific adapters for each container (syringes, bags, vials, bottles, infusers, cassettes, etc.) are already known on the market. These adapters must be introduced into respective adapter supports before starting a batch of preparations. Spanish Patent document ES2643119 B1 discloses an example of an adapter and a support for a dosing machine. These supports ensure that the dosing point of the containers is always in the same place, allowing easy automation of the dosing procedure.

A typical container loading process involves removing the container adapters from the fixed supports of the machine, introducing the containers into the adapters, then placing the adapters, with the containers therein, back on the machine supports. Another process is to directly place the containers on the adapters, with the adapters already placed in their machine supports.

A problem with medical product preparation machines equipped with worktop is that the process of loading containers into the machine for filling is a slow process. Also, depending on the type of container, this process can be difficult. This problem is even more relevant when loading a batch of containers, because containers must be placed on the adapters one at a time.

SUMMARY OF THE INVENTION

An object of the present invention is to provide a medical product preparation machine equipped with a worktop that allows containers to be loaded quickly into the machine and that also allows the correct fastening of the containers during their filling by automated or robotic means on the machine. The correct fastening of the containers is important due to the force that the robotic means of the machine exert on the containers during their filling.

Preferably, the machine of the present invention is a machine for dispensing medical products, more preferably, for dispensing intravenous medications, even more preferably non-cytostatic intravenous medications (for example, antibiotics or anesthetics).

More specifically, the present invention discloses a machine for the preparation of medical product that includes a worktop for receiving containers. The worktop comprises two or more holes, each of them intended to introduce an injection point belonging to a medical container to be filled. Said holes provide access to the inside of the machine so that the injection points of the medical containers remain inside for their filling by the machine, where the robotic or automated means of the machine for the filling of containers are preferably arranged. To facilitate the placement of the containers, the machine comprises a removable device for loading medical containers in the machine, the removable device comprising housings for said medical containers and removable fasteners to the worktop of the machine.

The removable device facilitates the introduction of the containers into the machine. As it is removable, it allows the device to be introduced first on the worktop and the containers to be placed subsequently in the device's housings intended for that purpose. In a non-preferred method of introduction, it is possible to first place the medical containers in the device housings, then place the device on the worktop of the machine. The removable device allows the introduction of the containers without the use of an individual support and an individual adapter for each of the medical containers, as well as the introduction of containers in batches. In addition, it allows a reduction in the effort and concentration that the operator needs for the correct loading of the containers.

The removable fasteners to the machine worktop of the removable device allow the device to be correctly fastened in the machine. Consequently, they allow the medical containers to be correctly fastened in the machine. This fastening is especially relevant during the filling of the containers, in which the robotic means of the machine exert a force on the containers that can move and rotate the containers. These fasteners allow the removable device to be fastened to the machine worktop regardless of the type of medical container intended to be placed on the removable device.

In the context of this invention, the expressions "lower" or "interior" of the worktop designate the face of the worktop located inside the machine, where the robotic means for filling are located, being also the closest part to the robotic means for filling the containers; while the expressions "upper" or "exterior" designate the face of the worktop located towards the outside of the machine. The worktop surface is generally horizontal.

Preferably, the fasteners of the device comprise claws. Said claws are preferably arranged in a lower portion of the device. Each of said claws is L-shaped, defining a proximal portion of the claw and a distal portion of the claw. Said claws are intended to be introduced into said holes. The proximal portion connects with the device, while the distal portion ends at the free end of the claw. The distal portion of the claw makes a dimensional interference with a lower portion of the worktop. The distal portion of the claw is located below the worktop after the device's claws have been introduced into the hole in the worktop. This placement allows the claws to make a dimensional interference with the lower portion of the worktop, preventing upward movement of the device once the device is placed in the machine. In this way, the movement of the device in the Z axis is limited.

Preferably, the proximal portion of the claw has a length greater than the thickness of the main horizontal surface of the worktop. This allows its distal portion to be below said worktop.

Preferably, a set of said holes are arranged in a line, and said L-shapes of the claws are arranged according to a plane parallel to said line.

Preferably, the fasteners of the device comprise protruding teeth for dimensional interference with conjugated elements of the worktop. Said conjugated elements on the worktop are preferably protrusions from the worktop of the machine. The protrusion-protrusion interference allows limiting the movement of the device in one direction.

More preferably, the protruding teeth of the device are alternately located along the lower portion of the device. Even more preferably, the protruding teeth of the device are staggered protrusions along the rear of the lower portion of the device. Preferably, the protrusions on the worktop are teeth. Preferably, the teeth of the device are placed behind and aligned with the protrusions of the worktop or machine. By arranging the teeth of the device behind the teeth of the worktop, the movement of the device in the Y axis is blocked, preventing it from moving towards the front of the worktop. Preferably, the worktop protrusions are located alternately, i.e., leaving spaces between protrusions. These spaces allow the passage of the protrusions of the device through them, and facilitates said rear and aligned placement to perform the interference. Preferably, the protrusions of the device are also staggered, separated by spaces or protrusions, for the same reason.

Preferably, the worktop protrusions are arranged on an elongated support of the machine worktop.

Preferably, the fasteners of the device comprise a recess for locking therein a retainer of the machine. More preferably, the recess of the device is located at the rear of a lower portion of the device. In other words, the recess is arranged behind when the device is placed in the machine. The recess may be in the form of a groove. The retainer of the machine may, preferably, be arranged downstream of a hole in the machine. The recess of the device may have larger dimensions than the retainer of the machine. It is also possible that they preferably have the same dimensions. These dimensions facilitate the introduction of the retainer in the groove once the device is placed on the machine worktop.

The locking of the retainer in the groove prevents the device from moving along the X axis, i.e., in a direction parallel to the device and also parallel to the direction of the work lines of the worktop, removing a degree of freedom to the device and facilitating its fastening.

Preferably, the retainer comprises a guide, the retainer being movable along said guide. The guide allows the retraction movement of the retainer in the Y axis. I.e., towards the rear of the device. This movement makes it possible to create space in front of the retainer in order to align the recess of the device with the retention device. The groove of the device is then arranged in front of said retainer. In this way, the return movement of the retainer towards the front of the device causes the retainer to be introduced into the recess where it remains locked. More preferably, the retainer comprises elastic means for recovering the position. The elastic means for recovering the position make it possible to automate this second movement.

Preferably, the retainer is movable in a direction perpendicular to that of the "L" of said claws.

Even more preferably, the machine comprises more than one retainer, for fastening more than one removable device of the machine.

Preferably, the retainer is arranged to the left of a work line of the machine. This layout is more comfortable for the right-handed operator. Alternatively, the retainers are arranged to the right of the machine fastening support.

The interconnection of the fasteners of the device with the machine allows the device to be correctly fastened during the filling of the containers, avoiding the movement of the injection points of the containers during their filling. The fasteners of the device allow it to be fastened on the machine in three directions, corresponding to the coordinate axes X, Y and Z. The corresponding turns around said axes (MX, MY, MZ) are also prevented. The machine could comprise fastening means on one or two of these three axes, although it preferably comprises fastening means on all three axes.

Preferably, the machine comprises an elongated support for fastening a device for loading containers. Said support is arranged on the worktop of the machine and comprises the protrusions of the worktop. Said support also comprises said retainer. The fasteners of the worktop, i.e., the protrusions of the worktop and/or the retainer, are preferably arranged on said support. This elongated support allows a removable device to be placed on it. The elongated support may be placed on the worktops of any type of machine for preparing medical products. This allows to use a removable device with the fasteners described above in this application, on existing machines.

Preferably, the elongated support is arranged in an area behind the holes of a line of work of the machine, or line of holes. This position makes it easier for the operator to place and remove containers, although other arrangements than the one mentioned are also possible. Preferably, the retainers are arranged on the left side of the elongated support. The position of the retainer in the elongated support makes it easier to place the devices first on the right, then on the left so that, when unloading the devices, the devices on the left are removed first, leaving the retainer accessible for said removal. Alternatively, this process could be done in reverse.

The present invention also relates to the device for loading medical containers in a machine for the preparation of medical products as described above. Preferably, the fasteners to the machine worktop are arranged in a lower portion of the device. Even more preferably, the fasteners comprise protruding teeth, more preferably arranged on the rear face of the device, more preferably being arranged alternately along the device. The removable device may be a device for loading any type of medical container, including, but not limited to, bags, syringes, infusers, cassettes, or any other known type of medical container.

The present invention also provides a support for fastening a removable device in a machine for the preparation of medical products such as that described above. Said device comprises a retainer and protruding teeth. Preferably, this support is an integral part of the worktop of the machine.

The present invention also provides a method for introducing a device for loading medical containers into a machine such as that described above. This method comprises the sequential steps of:

positioning the device on the worktop of the machine by introducing the claws of the device into the respective holes in the worktop, and moving the device in a direction parallel to the worktop until the device's claws are interlocked in the worktop, preventing movement of the device in the direction perpendicular to the plane that defines the worktop, a direction that may preferably coincide with the vertical direction.

This method for introducing the device offers the advantage that the device remains interlocked in the worktop because the distal portion of the claws is below the worktop and the device is above the worktop. This prevents it from moving vertically, i.e., in a direction perpendicular to the plane of the worktop. This interlocking removes a degree of freedom from the device in the Z axis and facilitates its fastening for the correct filling of the containers.

Preferably, it further comprises the sequential steps of:
moving the retainer while retracting it,
positioning the recess of the device in front of the retainer of the machine,
moving the retainer of the machine until it penetrates into the recess of the device.

Retracting the retainer makes room for device placement and allows subsequent steps to be performed. This allows force to be exerted in order to displace the retainer and compress it through the device.

Retracting the retainer is preferably carried out by pushing the device onto the retainer. This allows the movement to be carried out in conjunction with the placement of the device on the worktop. Preferably, retracting the retainer is achieved by moving the device in a direction perpendicular to said direction parallel to the worktop. Preferably, this movement is carried out before carrying out said displacement of the device in a direction parallel to the worktop. In this movement, the device moves towards the rear of the machine. Preferably, in this movement, the teeth of the device are located behind the teeth of the worktop.

Preferably, the displacement of the retainer of the machine until it penetrates into the groove of the device is carried out automatically by the action of elastic elements when the recess and the retainer are aligned.

In a particularly preferred manner, said positioning of the recess opposite the retainer, and said displacement of the device in a parallel direction, are carried out simultaneously by means of the same movement of the device. This causes a simultaneous interlocking along several axes.

After interlocking the claws, the device is stationary in the vertical axis (or Z axis). At the same time, when the retainer penetrates into the recess, a fastening is produced that prevents movements along the Y axis. To that end, preferably, the retainer of the machine comprises elastic elements for recovering the position, so that the elastic means are compressed during the retraction of the retainer and are decompressed when the recess and the retainer are aligned, the elastic elements for recovering the position moving the retainer of the machine towards the front of the machine, being automatically interlocked in the recess of the device without the need for a manual step of moving the retainer.

More preferably, the movement of the retainer of the machine is carried out by resting the device on the retainer.

Optionally, the method may comprise an additional step, immediately after the aforementioned step of placing the device on the worktop, that of moving the device in a direction parallel to the line of work of the machine, so that the claws of the lower portion of the device touch the wall of a hole in the worktop. This additional movement makes it possible to ensure correct placement of the device, making it easier for the machine teeth and device teeth not to collide during subsequent steps.

Preferably, the movement of the device in a direction parallel to the worktop occurs in a direction of alignment of the holes in the worktop. Preferably, said step of moving the device in a direction parallel to the worktop causes a proximal portion of the claws on the lower portion of the device to touch a lateral wall of the hole. Also preferably, said displacement step causes the proximal portion of the claws to contact another lateral wall of the hole.

As used herein, "medical container" and its plural, refer to any type of container used in healthcare to store, prepare or dispense medications (for example, intravenous medications, such as non-cytostatic intravenous medications, among others, antibiotics and anesthetics) and other solutions used in intravenous treatments (such as physiological solutions, saline solutions or food solutions). "Medical product" and its plural are used in this document to refer to these drugs and other solutions.

As used herein, "dosing point", "injection point" and their plurals refer to the point of the medical container from which the dosing of the same is carried out, i.e., the point through which the drug (preferably intravenous drugs, such as non-cytostatic intravenous drugs, including, but not limited to, antibiotics and anesthetics) or intravenous treatment solution (such as physiological solutions, saline solutions or food solutions) is introduced into the medical container.

As used herein, "rear" or "behind" refers to the part of the device or machine that is located furthest from the operator, while "front" is the part that is closest to the operator. In machines such as dosing machines, adapters and containers are usually placed in front of the holes in the machine worktop.

BRIEF DESCRIPTION OF THE DRAWINGS

For better understanding, by way of explanatory but non-limiting example, several drawings of an embodiment of the present invention are attached.

DETAILED DESCRIPTION OF THE PREFERRED EMBODIMENTS

Figure 1:
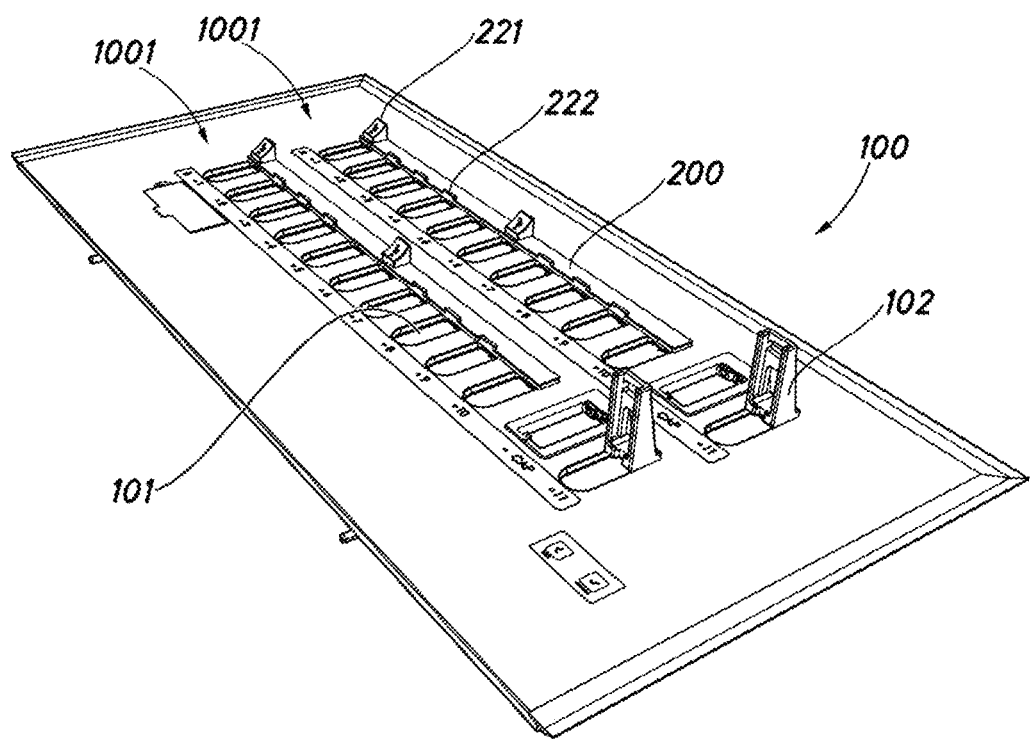
FIG. 1 shows a perspective view of a worktop of a machine for the preparation of medical product according to the present invention.

FIG. 1 shows a worktop 100 of a machine 1000 for preparing medical products, specifically a worktop of a dosing machine that doses medical products in medical containers. This worktop 100 is shown separate from the machine for illustrative purposes, and it should be understood that this worktop is part of the machine 1000 for preparing pharmaceutical products.

The worktop 100 comprises holes 101 for loading medical containers, more specifically for introducing dosing points belonging to medical containers into them. These holes give access to an interior cavity or cavities of the machine 1000. FIG. 1 shows a worktop 100 with two lines 1001 of holes 101, corresponding to two work lines 1001 of the machine 1000. Multiple lines allow filling several batches of containers at the same time. The machine may comprise a different number of work lines, or a different number of holes in each line.

The worktop 100 of the machine 1000 comprises two elongated supports 200 for fastening the loading device 3 for loading medical containers, one for each work line 1001 of the machine. Each elongated support 200 comprises an actuator or retainer 221 and protruding teeth 222 for interconnection with the device 3. These protruding teeth 222 are located alternately along the length of the elongated support 200. This elongated support 200 is an element of the worktop 100 of the machine that facilitates the fastening of the device 3 to the rest of the machine. In the example shown, each elongated support 200 comprises two retainers 221, allowing the fastening of two loading devices 3 on each support 200. This allows work with two batches of syringes in each work line 1001 of the machine. The retainers 221 are shown located on the left side of the elongated support 200.

The holes 101 also allow to introduce individual supports 102 for medical container adapters. The worktop 100 of the example is shown with two individual adapter supports 102. These individual supports 102 are located at one end of the worktop 100, one per work line 1001. The two supports 102 of the exemplary embodiment allow loading a source container. This source container is a container with the drug to be injected or dosed into the medical containers to be filled. Robotic means of the machine extract the drug from the source container and inject it into the containers to be filled. Furthermore, the rest of the holes 101 are shown without said individual supports 102 and are located next to one of the aforementioned elongated supports 200. In accordance with the present invention, the containers may be introduced in batches, being placed in the loading device before placing the loading device in the machine by fastening it on the elongated supports 200 of the machine, or vice versa.

Figure 2:
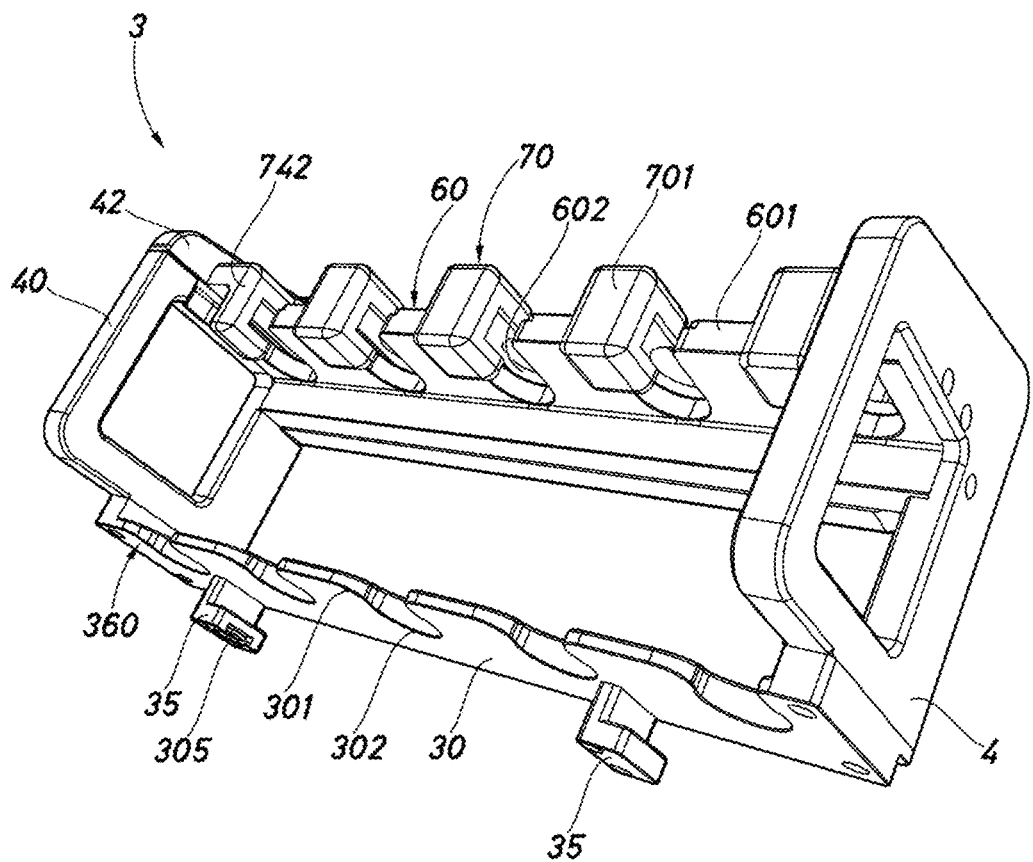
FIG. 2 shows a first perspective view of a device for loading medical containers according to a first embodiment of the machine.
Figure 3:
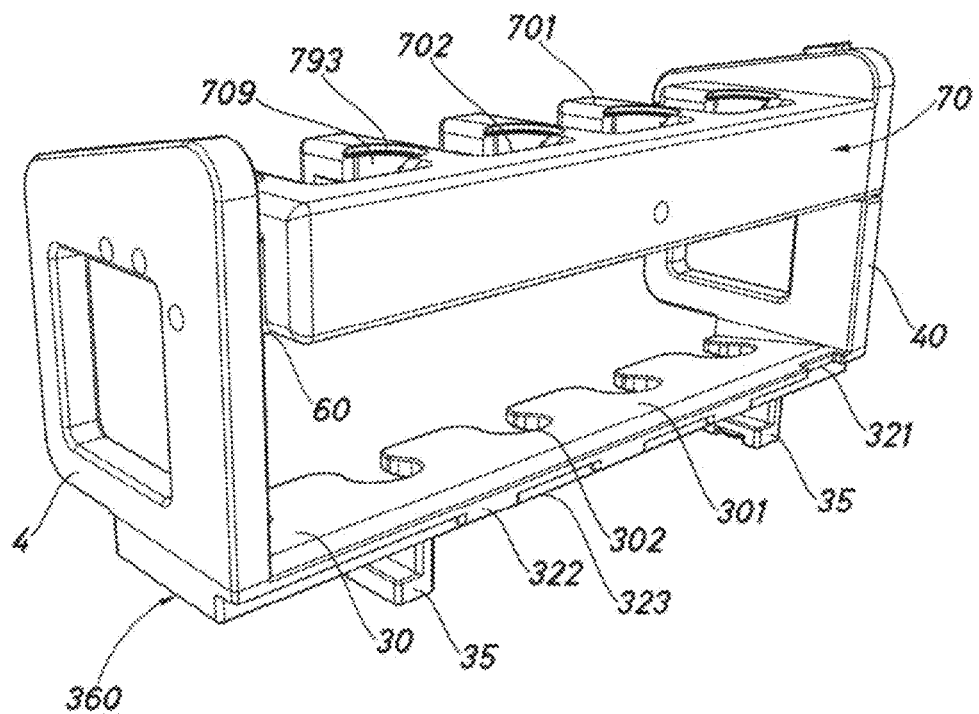
FIG. 3 shows a second perspective view of the device of FIG. 2.

FIGS. 2 and 3 show two perspective views of a device 3 for loading syringes in the machine according to a first embodiment of the machine. Syringes typically comprise a plunger and a body, also called a barrel. Syringes comprise an injection or dosing point at one end of the syringe. This dosing point may be of the Luer-Lock type. The body of the syringe comprises a support tab. This tab is also called a flange. Also, the plunger has a base.

FIG. 2 shows the device 3 from its front face while FIG. 3 shows the device from its rear face.

The device 3 comprises a fixed portion 360, which in turn comprises a fixed lower portion 30 and a fixed upper portion 60. The lower portion 30 and the upper portion 60 comprise respective housings 302, 602 for housing syringes and protrusions 301, 601 for separation between said housings 302, 602. Each of the housings 302 of the lower portion 30 is aligned with a respective housing 602 of the upper portion 60. When placing a syringe in the housing 602, the body of the syringe is located inside the pair of housings 302-602, the tab resting on the upper portion 60 of the device, the syringe dosing point being located below the lower portion of the device 3 in order to facilitate the filling of the syringe by the robotic means of the machine. The upper portion 60 also comprises a first rectangular or U-shaped step (not shown) that facilitates the support of a syringe tab. The rectangular or U shape of the step also serves as an anti-rotation system during the filling of the syringe, hindering and/or preventing the rotation of the tab and, therefore, the rotation of the syringe.

The device also comprises a movable portion 70. The movable portion 70 of the example is arranged above the upper portion 60 of the fixed portion 360 and is movable in a direction parallel to the fixed portion 360. This movable portion 70 is movable in a direction parallel to the fixed portion 360. The movable portion 70 comprises recesses 702 for placing syringes inside, protrusions 701 for separation between said recesses 702, and housings 709 for syringes. In the device of the machine of the example, the housings 709 are arranged inside the aforementioned recesses 702 of the movable portion, on one side of the separation protrusions 701, which makes it easier for said housings to become recesses in the direction of movement of the movable portion 70. The recesses 702 have dimensions greater than the dimensions of the housings 302, 602. The protrusions 701 comprise interlocking claws 742 for locking them to the upper portion 60 of the device 3. The protrusions 701 comprise interlocking claws 742 at their ends that receive combined parts of fixed portion 360. These claws 742 are locked to the upper portion 60 of the device 3, preventing relative movements in directions other than the sliding direction and between the fixed portion 360 and the movable portion 70. The housings 709 have a semi-circular shape to house syringes. The dimensions of the housings 709 are such that syringe plungers do not contact the housings 709. The edges of the housings 709 also comprise a step 793 or a recess. This step 793 makes it easy to verify that the syringes are empty before they are filled. It is customary to depress the syringe plunger prior to filling to ensure that there is no initial air in the empty syringe. This second step allows positioning the base of the syringe plunger at the same height or slightly below the head after depressing the plunger. This step 793 makes it easy for the operator to visually identify that the syringes have been checked to ensure that they are empty. If this verification had not been made, the base of the plunger would protrude above the head. The movement of the movable portion 70 may be to the right or to the left of the device.

The device 3 also comprises two lateral handles 4, 40 on its sides. The movable portion 70 comprises a lateral wall 42 on one of its sides. Said lateral wall 42 is aligned with the handle of the device 3. An advantage of the handles 4, 40 is that they make it easy for an operator to grip the device.

In the context of this patent, it should be understood that device 3 could be a device for syringes with a different configuration, different housings, and not include a moving portion, an anti-rotation system or other characteristics described for housing syringes. For example, the device 3 could be a device for any other type of medical container, such as bags or infusers, etc., as well as having other elements than those mentioned.

Device 3 comprises fastening elements 322, 323, 35, 321 for fastening to a machine for the preparation of medical product. In the exemplary embodiment shown, these fasteners are arranged in the lower portion of the device. These fasteners comprise protrusions 322, recesses 323, claws 35 and a recess 321.

The recesses 323 of the device 3 are teeth intended to make a dimensional interference with conjugated elements of the machine, specifically with protrusions 222 of the elongated support 200 of the worktop 100 of the machine. These recesses 323 are located alternately with protrusions 322 along the lower portion 30 of the device 3. This allows their dimensional interference with respective protrusions or teeth 222, also located alternately along the elongated support 200 of the machine.

The claws 35 have an L-shape, with a proximal portion of the claw 35 and a distal portion of the claw 35. This shape allows the distal portion of the claws 35 to be below the wall of the worktop 100 after placement of the device 3 on said worktop 100. During the placement of the device 3 on the worktop 100, the claws 35 are introduced into holes 101 of the worktop 100, and the device is subsequently moved until the distal portion of the claws 35 is below the wall of the worktop 100. In this arrangement, the claws 35 prevent the possible removal of the device 3 from the machine by means of a vertical movement upwards, i.e., perpendicular to the plane formed by the worktop or according to the coordinate axis Z. The length of the proximal portion of the claw 35 is such that it allows its distal portion to be below the worktop 100. Additionally, one of the claws comprises a radio frequency identification (RFID) tag 305 for the correct identification of the device.

Figure 4:
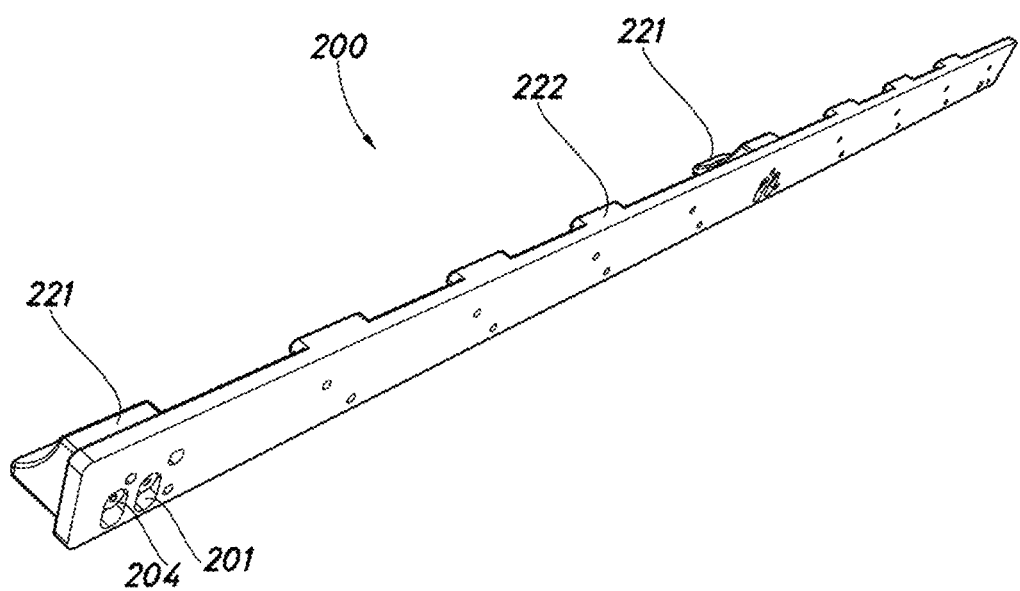
FIG. 4 shows a perspective view of the elongated support of FIG. 1.

FIG. 4 shows an elongated support 200 for fastening the device 3. The elongated support 200 shown comprises two retainers 221 and two sets of teeth 222 located along the elongated support 200. This allows the placement of two devices 3 for loading containers on the same elongated support 200. As can be seen, the elongated support 200 comprises two guides 201 in which two through elements 204 of the retainer 221 are located, so that the retainer 221 is movable along said guides 201.

Figure 5:
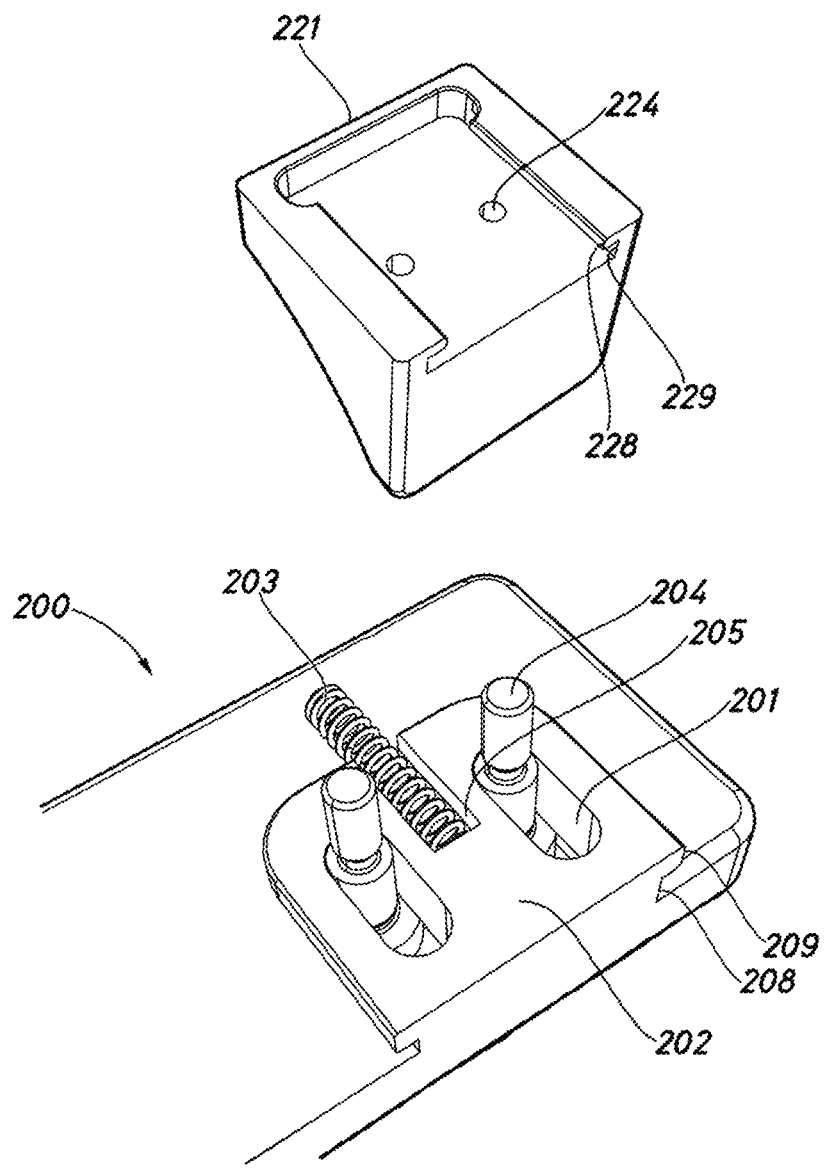
FIG. 5 shows an exploded perspective view of the retainer of the elongated support of FIG. 4.

FIG. 5 shows the retainer 221 and the elongated support 200 in an exploded view. As can be seen, the retainer 221 is arranged on a protrusion 202 of the support 200. The support also comprises a groove 205 in which a spring 203 is housed. This spring 203 is an elastic means for recovering the position. A compression movement on the retainer 221 allows it to be moved towards the rear of the support 200 thanks to the movement of the elements 204 along the guides 201. The spring 203 allows the retainer 221 to return to its original position after stopping such compression. The retainer 221 is locked in the elongated support 200 by dimensional interference between the protrusion 209 of the support and the recess 229 of the retainer 221, and between the recess 208 of the support 200 and the protrusion 228 of the retainer 221. The retainer 221 is also attached to the through elements 204 through the holes 224, although any type of attachment is possible.

Figure 6:
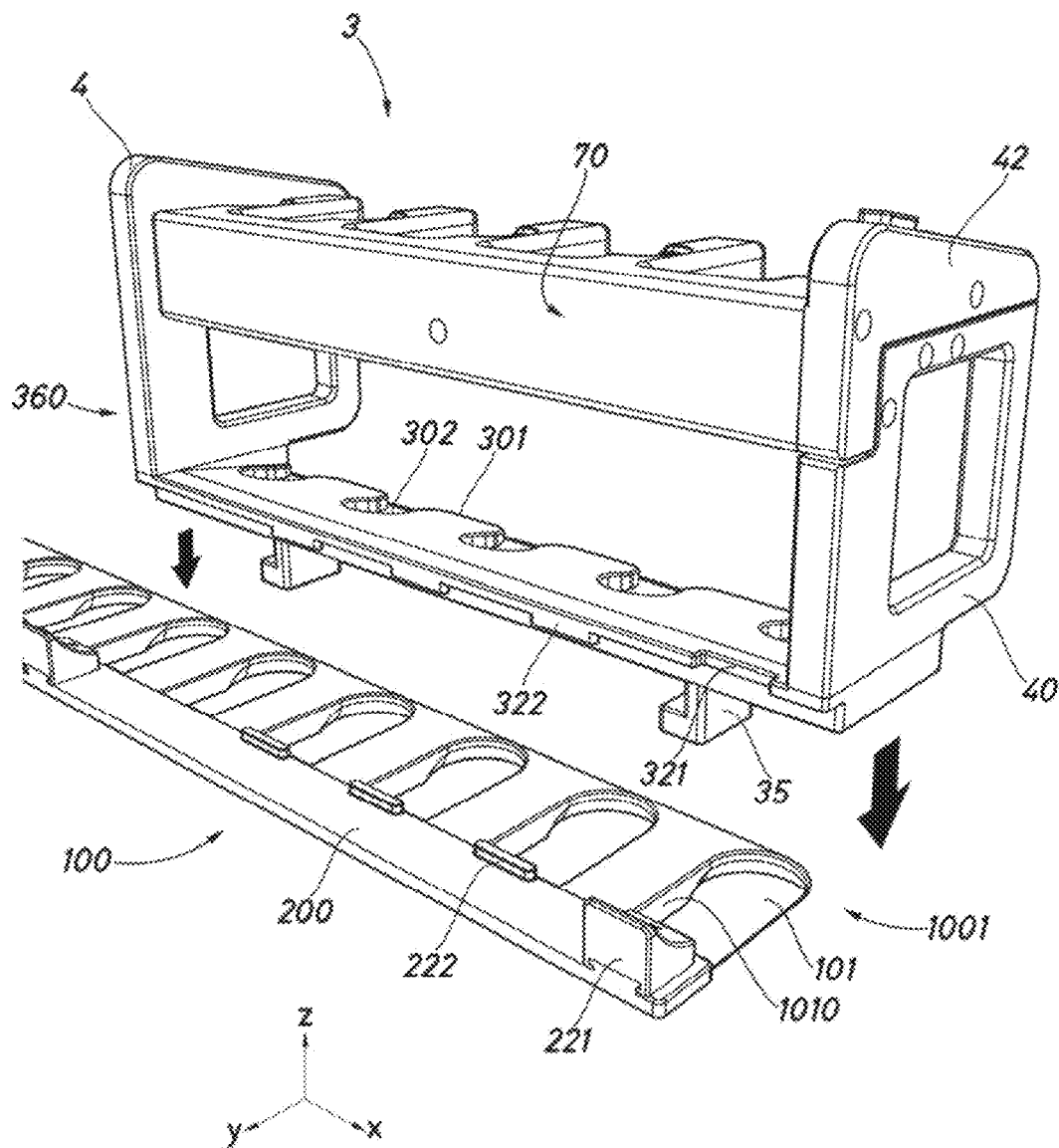
FIG. 6 shows the first step of the method for introducing the removable device of FIG. 2 into the worktop of the machine.

By arranging the recesses 323 of the device 3 behind the teeth 222 of the machine, the dimensional interference between the two prevents the movement of the device in the Y axis shown in FIG. 6. In other words, the device 3 is prevented from moving towards the front of the worktop. The dimensions of the teeth 322 may vary from those shown in device embodiment 3, and other thicknesses, sizes, and shapes may be used. A larger size gives the device greater robustness and greater fastening. However, in some cases the teeth 322 of the device may be shorter to facilitate loading and unloading of the device 3 in the machine. For example, in devices for loading other medical containers such as bags, a larger size of the teeth 322 of the device could prevent or hinder loading and unloading of the device in the machine when the injection points of the bags are in working position (i.e., in its position perpendicular to the machine worktop), allowing only the loading and unloading of the device in the machine with the injection points in a loading position that is not perpendicular to the machine worktop.

The recess 321 is in the form of a groove and is located at the rear of the lower portion 30 of the device 3. The recess 321 may preferably have dimensions greater than the retainer 221 of the machine. In this way, the introduction of the retainer 221 into the groove 321 is facilitated once the device 3 is arranged on the worktop 100 of the machine. This introduction of the retainer 221 into the groove 321 makes it possible to lock the retainer 221 in the groove 321, preventing the movement of the device 3 along the axis X, i.e., in a direction parallel to the device. Groove 321 is shown to be located at the rear left of device 3 (i.e., the part of the device that remains to the left of the operator once the device is in place on the machine), while retainer 221 is shown also arranged on the left side of the elongated support 200.

FIGS. 6 to 11 show a method for introducing from the rear of the machine, i.e., the part intended to be furthest from the operator once the device is placed in the machine.

FIG. 6 shows the arrangement of the worktop 100 and the removable device 3 before fastening the device 3 to the worktop. In these figures, the device 3 is shown without syringes for illustrative purposes, to improve understanding of the method for introducing the device into the machine. The method for placing the device on the worktop is independent of the presence or absence of medical containers and their type. However, typically, the loading of the devices on the worktop is done without the containers on them.

Figure 7:
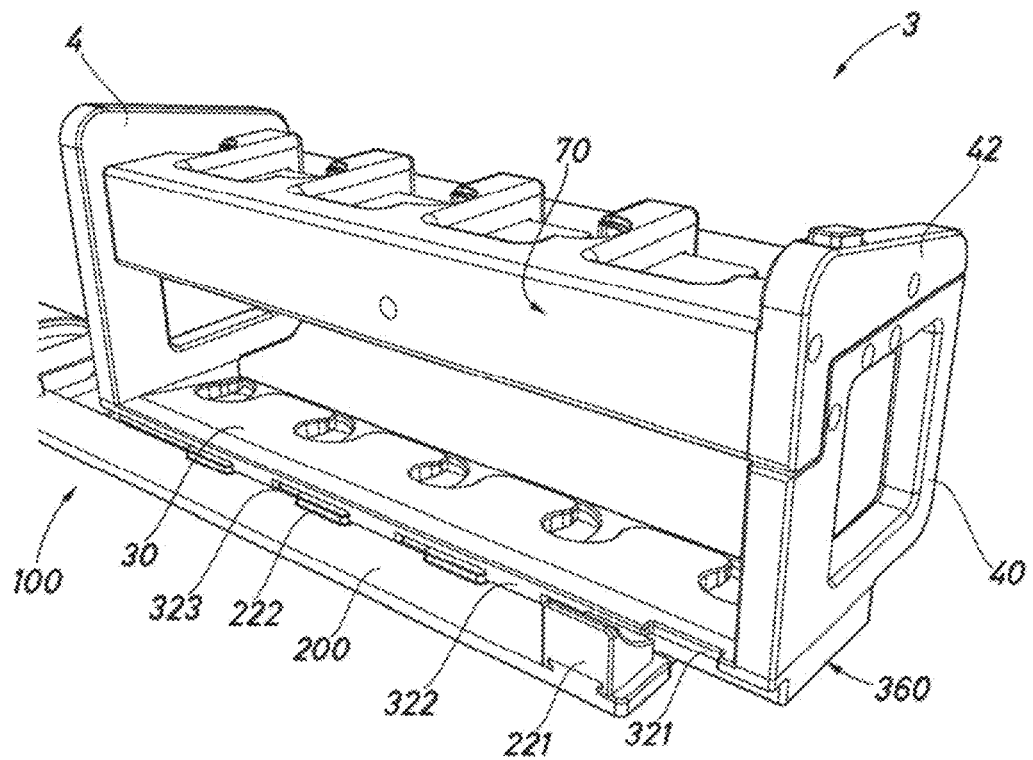
FIG. 7 shows the second step of the method for introducing the removable device of FIG. 2 into the worktop of the machine.
Figure 7:
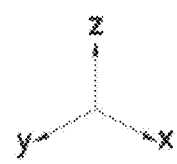

FIG. 7 also illustrates a first step of the method shown. In this first step, the device 3, which is removed from the machine, is positioned on the worktop 100, making a vertical downward movement (or in the Z axis). In this positioning, the claws 35 of the device 3 are introduced into the holes 101 of the worktop 100 of the machine. In other words, a movement perpendicular to the plane of the worktop 100 and towards the worktop 100 is performed on the device 3. FIG. 7 shows the positioning of the device 3 resting on the worktop 100 after its downward movement.

Figure 8:
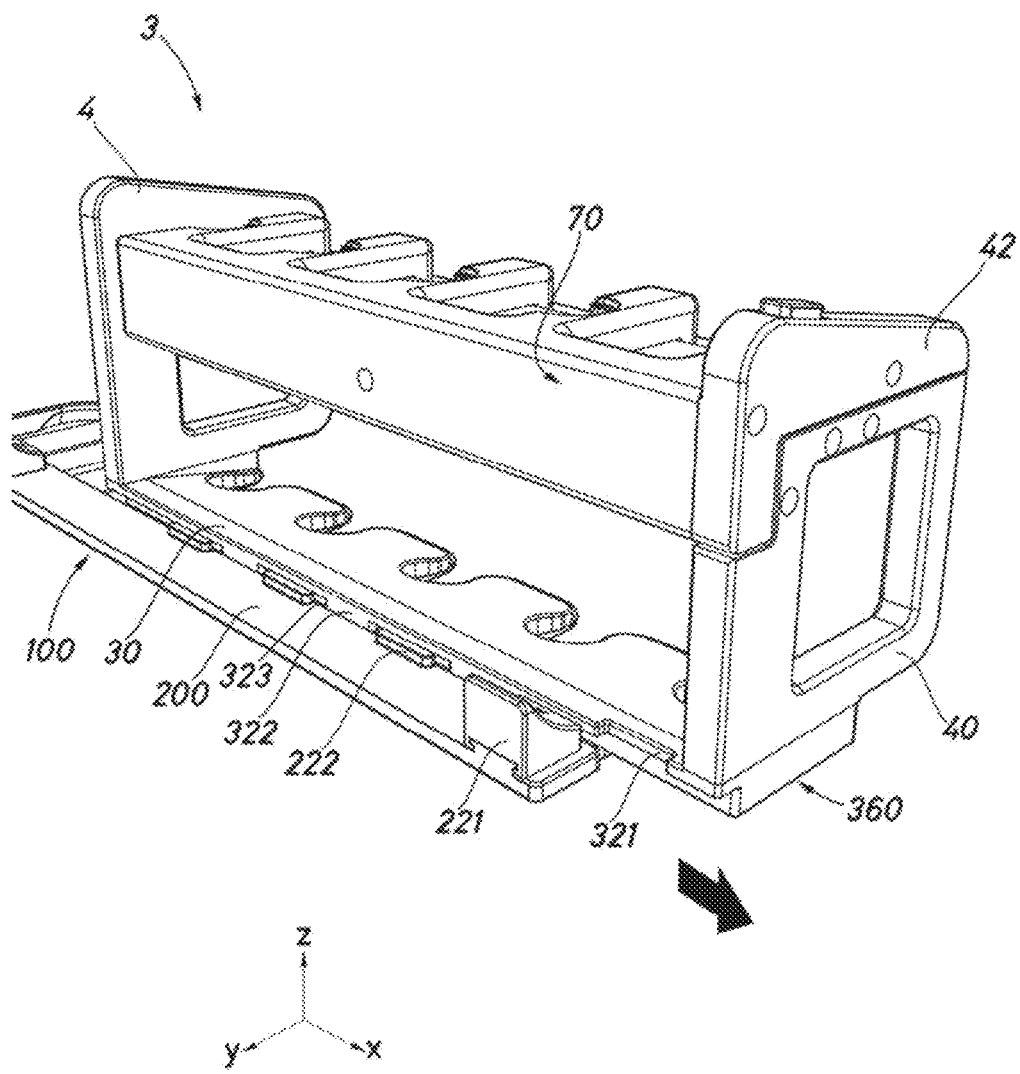
FIG. 8 shows the third step of the method for introducing the removable device of FIG. 2 into the worktop of the machine.

FIG. 8 shows a second step of the method of introduction. This step is optional and is intended to achieve the correct fit of the different parts in subsequent steps. This step is a complementary step of moving the device 3 laterally in a direction parallel to the device 3, so that the proximal portion of the claws 35 of the lower portion 30 of the device 3 touches a lateral wall of a hole in the worktop 100 in which the claws were introduced, which makes the movement stop. This movement makes it easier for the teeth 222 of the elongated support 200 of the machine and the teeth 322 of the device 3 not to collide in the next movement due to an incorrect initial positioning of the device during the previous vertical movement. The lateral movement performed is a movement in the direction of the position in which the retainer 221 is located. In FIG. 8, this movement was represented towards the left of the device 3 because the retainer 221 is arranged on the left of the elongated support 200. In an embodiment not shown, the retainer 221 may be located to the right of the elongated support 200. In this case, the movement made would be a lateral movement to the right.

Figure 9:
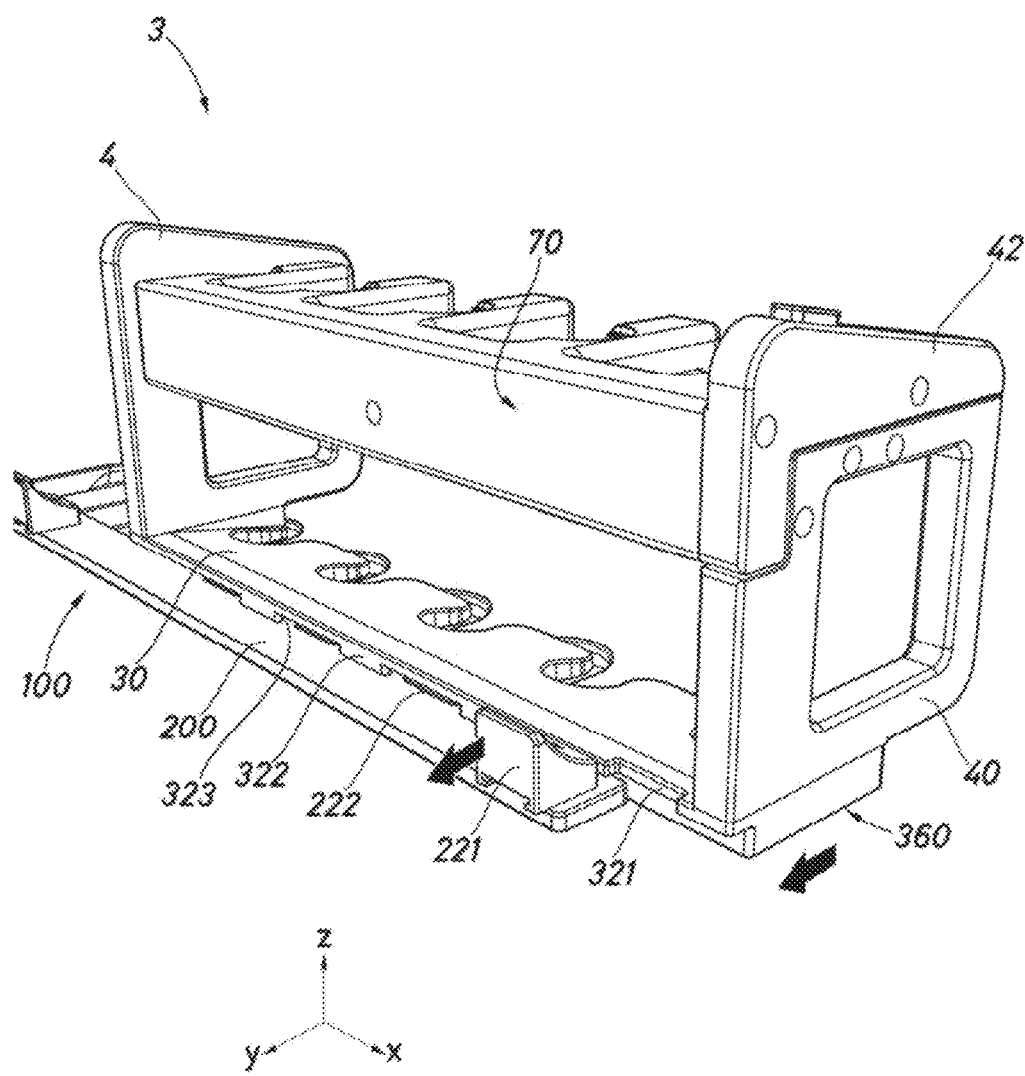
FIG. 9 shows the fourth step of the method for introducing the removable device of FIG. 2 into the worktop of the machine.

FIG. 9 shows the third step of the method of introduction. In this step, the device 3 is moved or pushed towards the retainer 221. In other words, towards the rear of the machine. Upon contact with the retainer 221, which is movable, the force exerted by the device displaces or compresses the retainer 221 in the direction of the Y axis (direction of movement). This compression, in turn, compresses the elastic recovery means of the retainer. Alternatively, compression of retainer 321 could be done manually. At the moment when the device 3 is pushed towards the rear of the machine, the teeth 322 of the device 3, which also move with the device 3, are located behind the teeth 222 of the elongated support 200 of the machine. In the position shown, the worktop protrusions 222 are aligned with the device recesses 323, which prevents the worktop protrusions 222 from colliding with the device protrusions 322. This alignment is facilitated thanks to the second step shown in FIG. 8.

Figure 10:
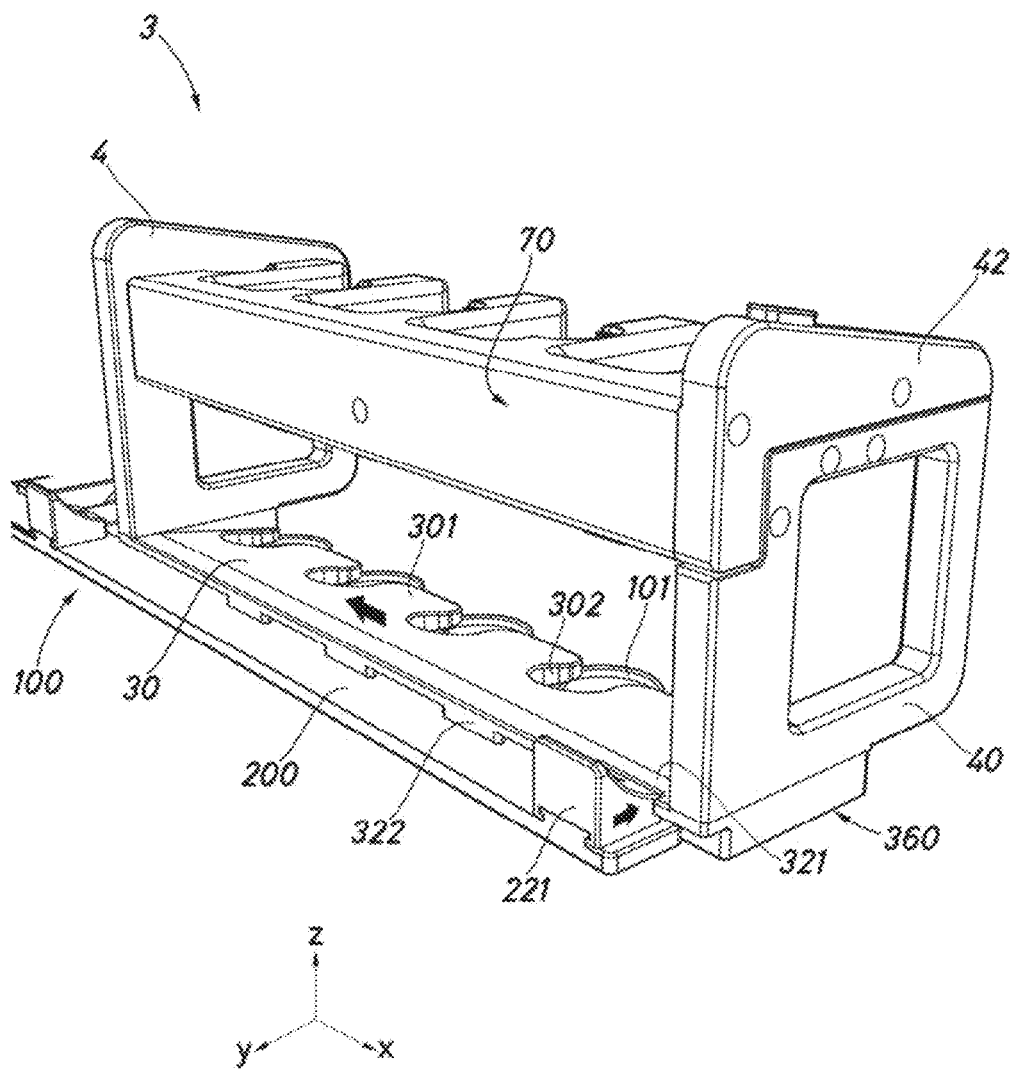
FIG. 10 shows the fifth step of the method for introducing the removable device of FIG. 2 into the worktop of the machine, with the device in the machine.

FIG. 10 shows the fourth step of the method of introduction. In this step, after the third step, the device 3 is moved laterally (on the X axis) in the opposite direction to the retainer 221 (i.e., in the same direction and in the opposite direction to that of the movement shown in FIG. 8) until the proximal portions of the claws 35 of the device 3 are in contact with the lateral walls 1010 of the holes 101 of the worktop 100 in which they have been introduced, and the distal portion of the claws 35 is below the plane of the worktop. In the case shown in the figures, this movement is to the right of the machine (left in the view). Thanks to this contact, the distal portions of the claws 35 are located below the worktop 100, making dimensional interference with the worktop, preventing the vertical movement of the device and fastening the device 3 in the machine in the coordinate axis Z.

This lateral displacement in the fourth step causes the retainer 221, previously compressed by contact with a lower portion 30 of the device 3, to be located opposite the recess 321 of the device 3. The contact of the retainer 221 with the free space of the recess 321 causes the spring of the retainer 221 to decompress, allowing the retainer 221 to recover its position and remain locked therein. This locking of the retainer 221 in the recess 321 prevents a lateral movement of the device 3 and removes a degree of freedom from the device, specifically in the X axis.

On the other hand, the lateral displacement in the X axis also causes the teeth 322 of the device 3 to be aligned and behind the teeth 222 of the elongated support 200 of the machine, preventing the movement of the device towards the front of the machine, removing one degree of freedom in the Y axis. Being aligned, the teeth 222 of the worktop are hidden by the teeth 322 of the device.

In other words, the method of introduction of the present invention allows to fasten a removable device of a medical product preparation machine in the machine itself, blocking the movement along three perpendicular axes X, Y, Z, where Z may be the vertical axis and X and Y may be two horizontal axes. Movement in the Z axis is impeded by the interference of the L-shaped claws with the worktop wall, in the Y axis due to the interlocking of the retainer, and in the X axis due to the fact that the protrusions of the device and worktop are aligned along said axis.

Figure 11:
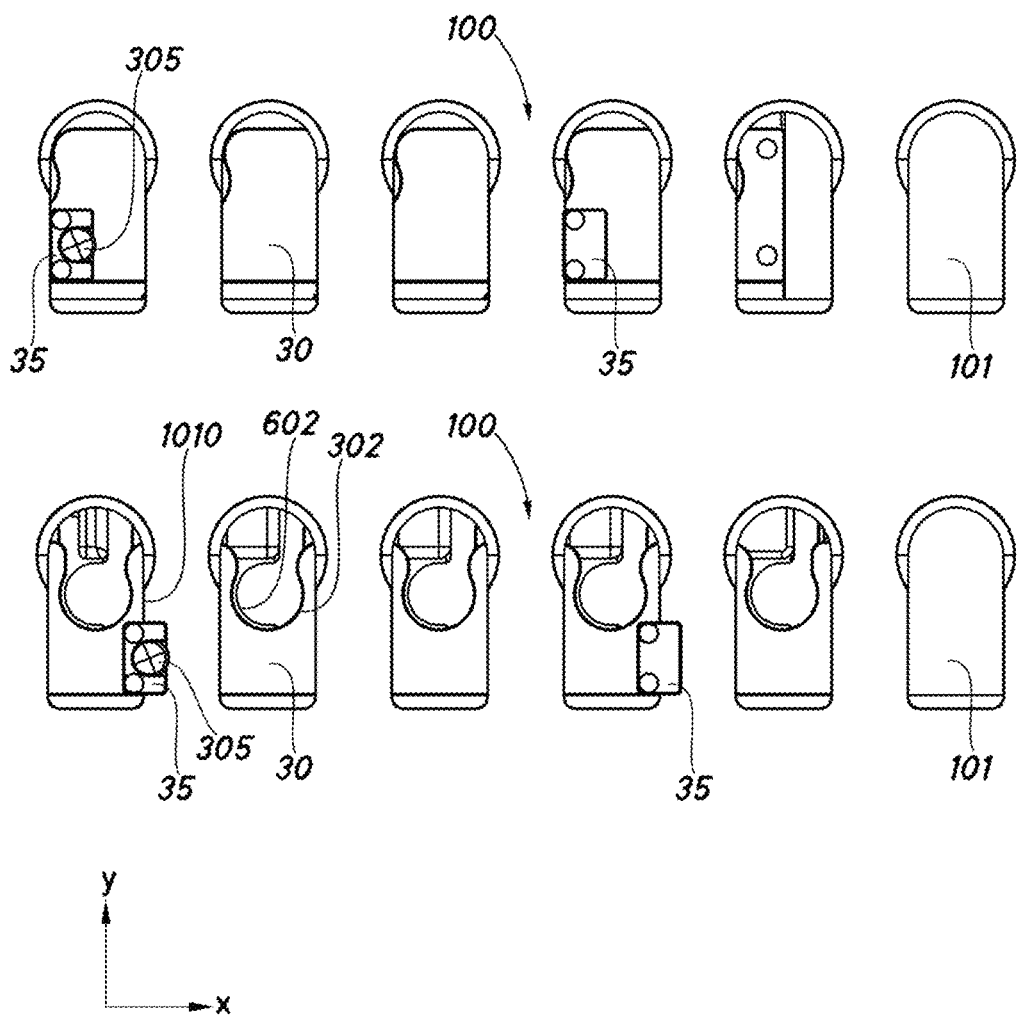
FIG. 11 shows a bottom view of the machine worktop after the second step and the fifth step of the method of introduction.

FIG. 11 shows the holes 101 of the machine worktop during two steps of the process of introducing a device 3 for loading syringes. The upper illustration shows a row of holes in the worktop 100 from a lower point of view after the second step of the method shown. As can be seen, each claw 35 of the lower portion 30 of the device 3 comes into contact with a lateral wall of the respective hole 101 in which they have been introduced, although the distal portion of the claw 35 remains inside the hole. The lower illustration shows the worktop 100 after the placement of the device 3 is complete, with the claws 35 interlocked in the lower portion of the worktop 100, preventing the vertical movement of the device 3, one of them comprising an RFID tag 305. In particular, it can be seen how the proximal portion of the claw 35 is in contact with a lateral wall 1010 of the hole, and the distal portion of the claw 35 is below a horizontal wall of the worktop. As can be seen, the housings 602, 302 of the upper portion 60 and of the lower portion 30 of the device 3 are aligned with the holes 101 of the worktop 100, allowing the robotic means of the machine to access the injection or dosing points of syringes located in said housings 602, 302.

Figure 12:
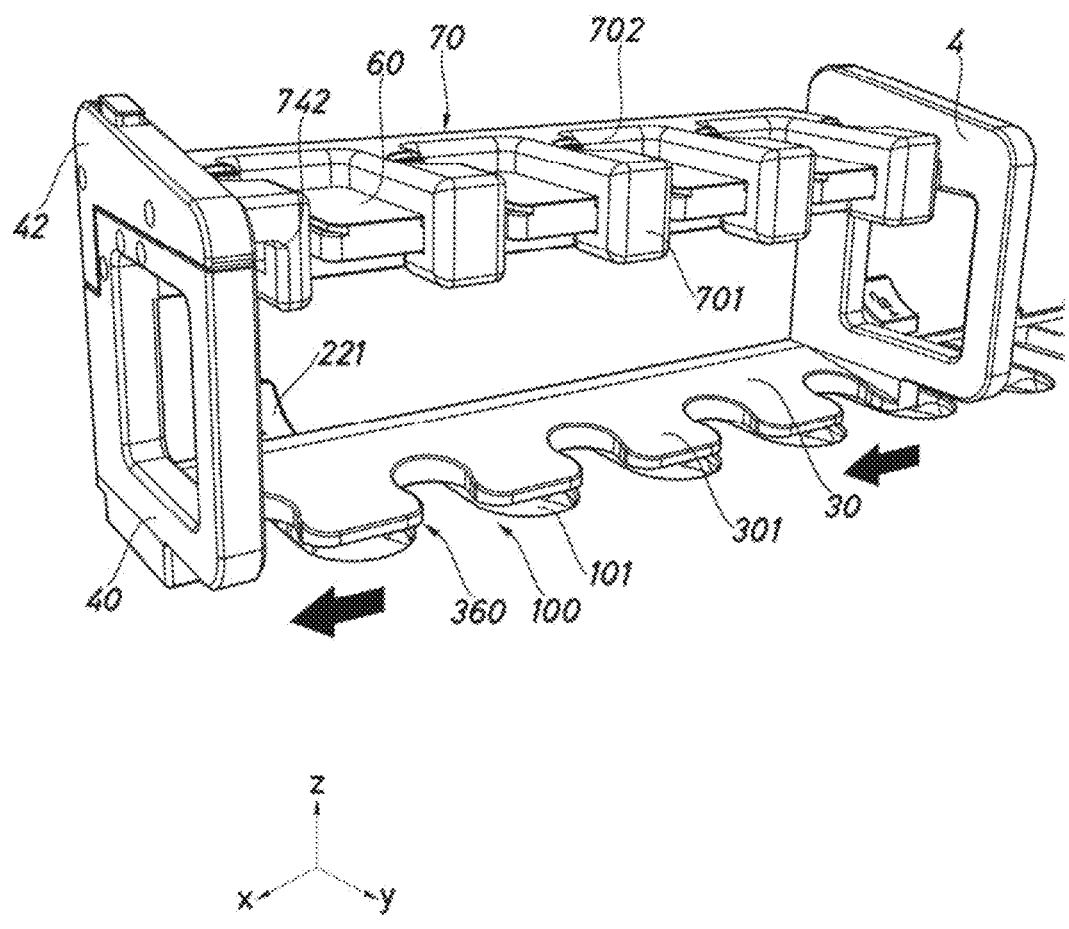
FIG. 12 shows the removal movement of the removable device from the machine.

FIG. 12 shows a method for removing the removable medical container loading device 3 from the machine. First, the medical containers are removed from the device. Secondly, the retainer 221 is compressed, displacing it from its locking position in the groove 321 of the device 3. This compression may be carried out by the operator by pushing the retainer 221 manually. The retainer 221 has a shape that makes it easy to remove it by pushing it, although the retainer could be of any other known type. Next, the device is moved laterally (movement marked by the arrows in FIG. 12) towards the opposite end where the claws 35 are interlocked, moving the claws 35 from their position under the worktop 100 to under the hole 101 and misaligning the aforementioned device and worktop protrusions. Finally, the device 3 is removed by moving it vertically.

Figure 13:
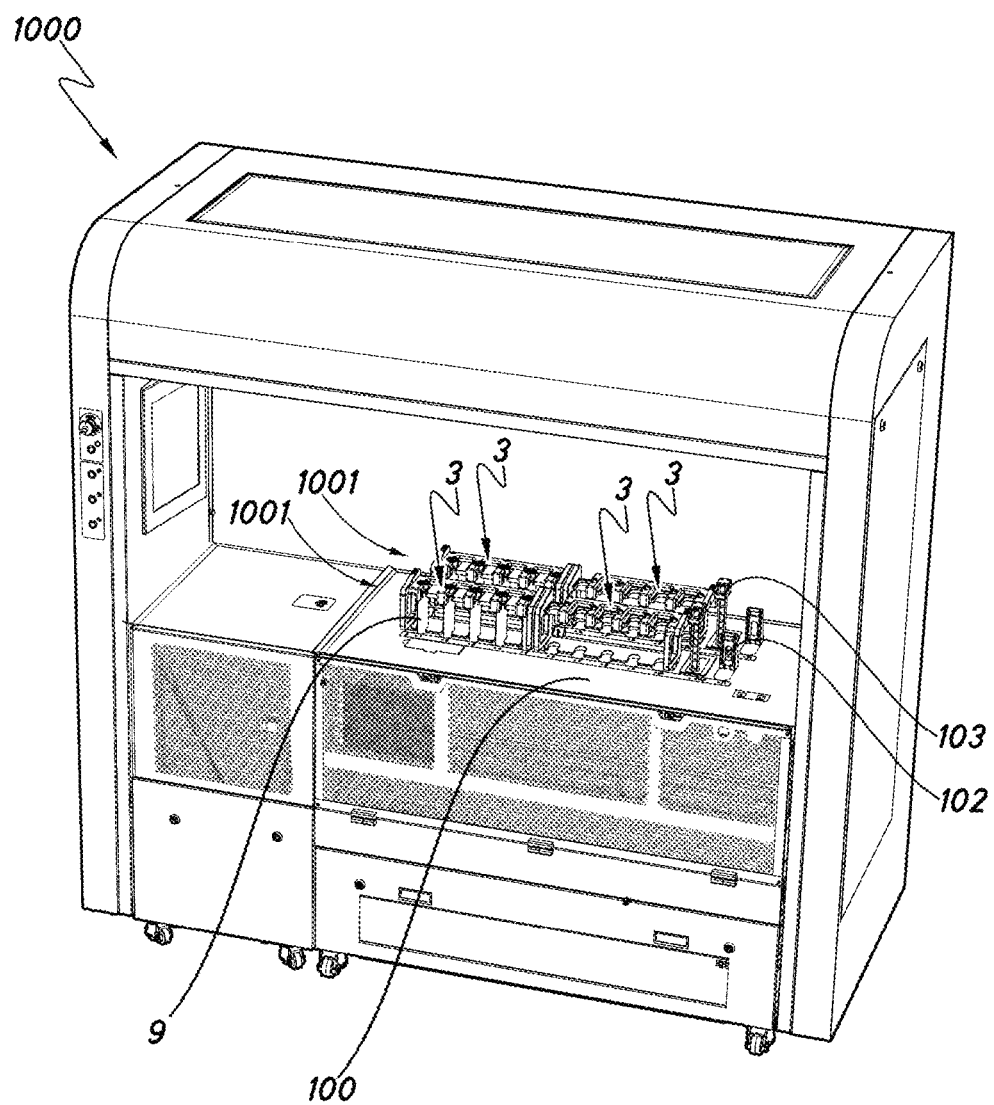
FIG. 13 shows a perspective view of a machine for the preparation of medical product according to the first exemplary embodiment, with the device for loading medical containers placed on the worktop of the machine.

FIG. 13 shows the machine 1000, with four devices 3 for loading syringes, placed on the worktop 100 of the machine 1000. In the figure, two work lines 1001 of the machine are shown, each of the two lines 1001 having two devices 3 placed on respective elongated supports 200 of the worktop 100. The devices 3 located to the left of the worktop are devices whose movable portion has the ability to slide to the left, while the devices 3 located to the right of the worktop are devices whose movable portion has the ability to slide to the right. This configuration is preferred to facilitate the opening of the moving portions once the devices 3 are placed on the worktop 100, which, in turn, facilitates the placement of syringes in the devices 3. The devices located on the left were represented with syringes 9 placed on top. FIG. 13 also shows a syringe cap dispenser 103 arranged on the worktop 100.

Figure 14:
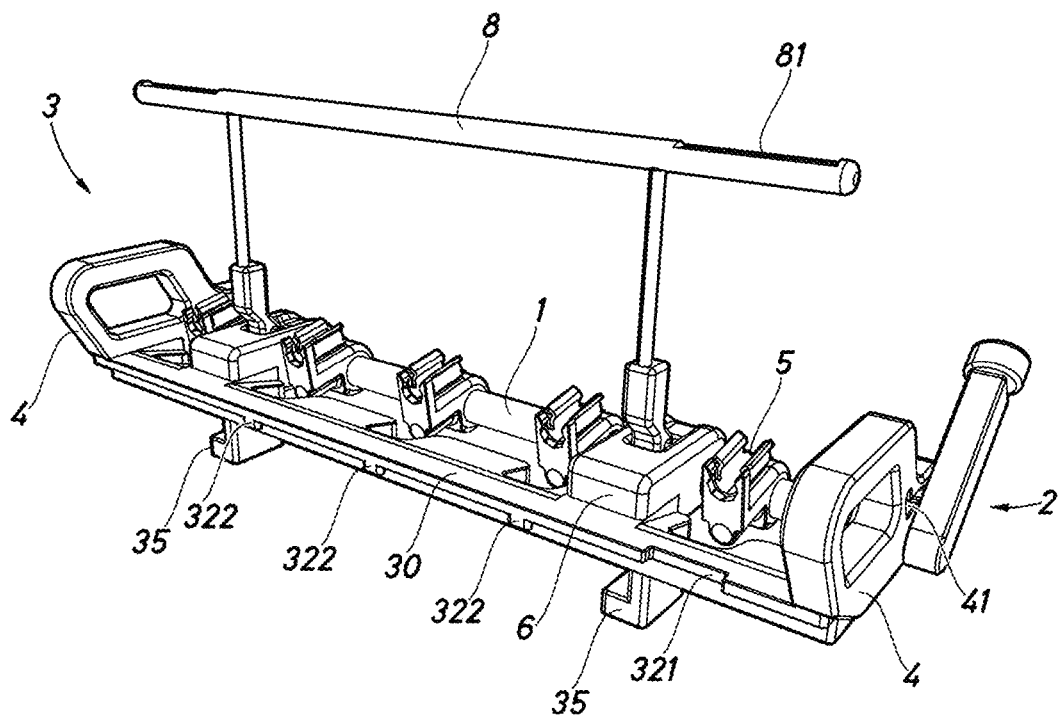
FIG. 14 shows a perspective view of a device for loading medical containers according to a second embodiment of the machine.

FIG. 14 shows the device of a second embodiment of a machine according to the present invention. In this case, the device is a device 3 for loading bags. This device comprises an shaft 1 with the capacity to rotate, a plurality of adapters 5 arranged on the shaft 1 with housings to house medical product bags, or injection points of said medical bags, the rotation of shaft 1 causing the rotation of the adapters 5, and two stops that limit the rotation of the shaft, said stops defining a position for loading bags by an operator and an operating position. The device 3 of FIG. 14 also comprises a guide 41 with a main curved area arranged in a handle 4 of the device and a lever 2 connected integrally to the shaft 1, the activation of the lever 2 causing the rotation of the shaft 1. This lever may be arranged to the right or left of the device. The device 3 also comprises a cross-piece 8 for hanging the medical product bags. The cross-piece 8 is arranged in connection structures 6 between the rear portion 30 and the shaft 1. The cross-piece 8 comprises gripping zones 81.

The device 3 for loading bags comprises fasteners analogous to those described for the device 3 for loading syringes shown in FIGS. 2 to 12. The method for introducing the device 3 into the machine 1000 is analogous to that already described. Analogous elements with the first exemplary embodiment were represented with the same reference numerals.

Figure 15:
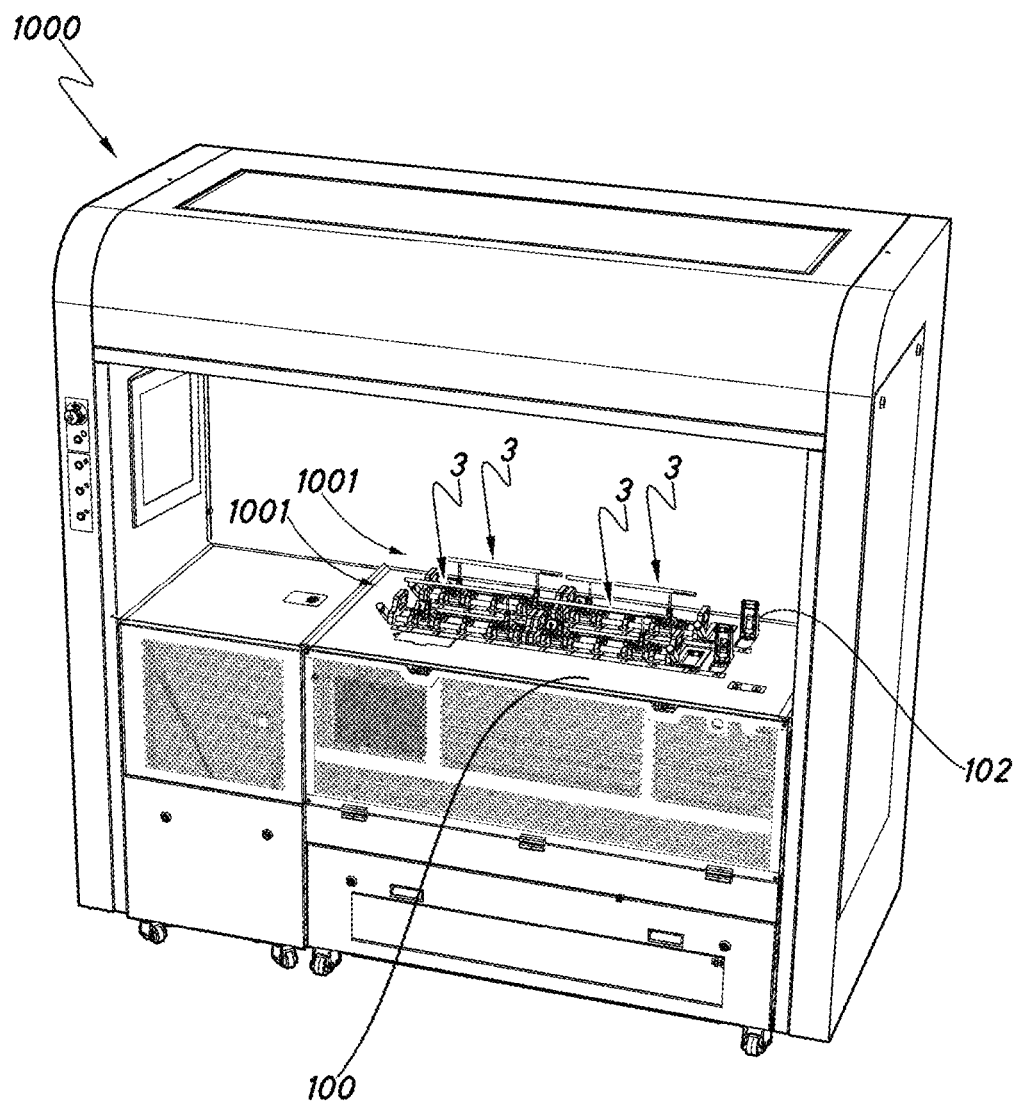
FIG. 15 shows a perspective view of a machine for the preparation of medical product according to the second exemplary embodiment, with the device for loading medical containers according to the second exemplary embodiment placed on the worktop of the machine.

FIG. 15 shows the machine 1000 according to the second embodiment, with four devices 3 for loading medical containers, specifically devices for loading bags, placed on the worktop 100 of the machine 1000. The figure shows two work lines 1001 of the machine, one of the two lines 1001 having two devices 3 placed on respective elongated supports 200 of the worktop 100. The devices 3 located to the left of the worktop are devices whose lever is arranged to the left of the device 3, while the devices 3 located to the right of the worktop are devices whose lever is arranged to the right of the device 3. This distribution is preferred to facilitate the actuation of the levers once the devices 3 are placed on the worktop 100.

Although the invention was described and represented based on representative examples, it should be understood that said exemplary embodiments are not in any way limiting to the present invention, so that any of the variations that are included directly or by way of equivalence in the content of the attached claims, should be considered included in the scope of the present invention.

What is claimed is:

1. A machine for the preparation of a medical product, said machine comprising a worktop for receiving containers, said worktop comprising a series of holes for the introduction in each of the holes of an injection point belonging to a medical container to be filled, said holes giving access to an inside of the machine, so that the injection points of the medical containers remain inside for filling of the medical containers by the machine, wherein the machine comprises a removable device for loading the medical containers in the machine, the removable device comprising housings for said medical containers and removable fasteners for fastening the removable device to the machine worktop, wherein the fasteners of the device comprise claws arranged in a lower portion of the device, each of said claws being L-shaped, defining a proximal portion of the claw and a distal portion of the claw, said claws being intended to be introduced into said holes, so that the distal portion of each claw makes dimensional interference with a lower portion of the worktop.

2. The machine, according to claim 1, wherein a set of said holes are arranged in a line, and said L-shaped claws are arranged according to a plane parallel to said line.

3. The machine, according to claim 2, wherein the fasteners of the device further comprise protruding teeth for dimensional interference with conjugated elements of the worktop, said conjugated elements of the worktop being protruding teeth of the worktop of the machine, wherein the fasteners of the device further comprise a recess for the interlocking therein of a worktop retainer, wherein the retainer comprises a guide, the retainer being movable along said guide, and wherein the retainer is movable in a direction perpendicular to that of the proximal portions of said claws.

4. The machine, according to claim 1, wherein the fasteners of the device further comprise protruding teeth for dimensional interference with conjugated elements of the worktop, said conjugated elements of the worktop being protruding teeth of the worktop of the machine.

5. The machine, according to claim 4, wherein the fasteners of the device further comprise a recess for the interlocking therein of a worktop retainer, the retainer comprises a guide, the retainer being movable along said guide, wherein the retainer comprises elastic means for recovering to an initial position, wherein the retainer is movable in a direction perpendicular to that of the proximal portions of said claws, and wherein the machine further comprises an elongated support for fastening said device for loading containers, said support being arranged on the worktop of the machine, said support comprising said protruding teeth of the worktop and said retainer.

6. The machine, according to claim 1, wherein the fasteners of the device further comprise a recess for the interlocking therein of a worktop retainer.

7. The machine, according to claim 6, wherein the retainer comprises a guide, the retainer being movable along said guide.

8. The machine, according to claim 7, wherein the retainer comprises elastic means for recovering to an initial position.

9. A method for introducing the removable device for loading medical containers in the machine for the preparation of a medical product according to claim 1, the method comprising the sequential steps of:
positioning the removable device on the worktop of the machine by introducing the claws of the device into the respective holes in the worktop; and
displacing the device in a direction parallel to the worktop until the claws of the device are interlocked in the worktop, preventing movement of the device in a direction perpendicular to a plane that defines the worktop.

10. The method, according to claim 9, wherein the fasteners of the device further comprise a recess for the interlocking therein of a worktop retainer, the retainer comprises a guide, the retainer being movable along said guide, further comprising the sequential steps of:

displacing the retainer of the machine while retracting the retainer;

positioning the recess of the device in front of the retainer of the machine; and displacing the retainer of the machine until the retainer penetrates into the recess of the device.

11. The method, according to claim 10, wherein the retracting of the retainer is achieved by displacing the device in a direction perpendicular to said direction parallel to the worktop, before carrying out said displacing of the device in a direction parallel to the worktop.

12. The method, according to claim 11, wherein the displacing of the retainer of the machine until the retainer penetrates into the recess of the device is carried out automatically by action of elastic elements when the recess and the retainer are aligned.

13. The method according to claim 9, wherein the displacing of the device in a direction parallel to the worktop occurs according to a direction of alignment of holes in the worktop.

14. The method, according to claim 9, wherein the displacing of the device in a direction parallel to the worktop causes the proximal portion of the claws of the lower portion of the device to touch a lateral wall of the corresponding hole.

\* \* \* \* \*